United States Patent
Melnichuk et al.

(10) Patent No.: US 6,747,067 B2
(45) Date of Patent: Jun. 8, 2004

(54) PROCESS FOR CONVERTING CELLULOSIC MATERIAL INTO LIQUIDS

(75) Inventors: Larry Jack Melnichuk, Burlington (CA); Karen Venita Kelly, Burlington (CA)

(73) Assignee: Woodland Chemical Systems, Inc., Burlington (CA)

( * ) Notice: Subject to any disclaimer, the term of this patent is extended or adjusted under 35 U.S.C. 154(b) by 0 days.

(21) Appl. No.: 09/799,342

(22) Filed: Mar. 6, 2001

(65) Prior Publication Data

US 2002/0035291 A1 Mar. 21, 2002

Related U.S. Application Data (60) Provisional application No. 60/187,166, filed on Mar. 6, 2000.

(51) Int. Cl.[7] .......... C07C 27/00; C07C 27/06; C07C 53/08; C07C 53/10; C07C 51/42
(52) U.S. Cl. .......... 518/702; 518/728; 562/607; 562/608; 564/60
(58) Field of Search .......... 518/702, 728; 562/607, 608; 564/60; 568/448, 449; 201/30

(56) References Cited

U.S. PATENT DOCUMENTS 3,874,116 A * 4/1975 White .......... 48/209
4,529,738 A * 7/1985 Sugier et al. .......... 518/700
536,482 A * 8/1985 Carcia .......... 502/5
4,670,570 A * 6/1987 Wegman et al. .......... 556/18

* cited by examiner

Primary Examiner—Richard L. Raymond
Assistant Examiner—Zachary C. Tucker
(74) Attorney, Agent, or Firm—Nancy E. Hill; Lynn C. Schumacher; Dowell & Dowell, P.C.

(57) ABSTRACT

A process for the production of oxygenated $C_2$ hydrocarbons from cellulose is disclosed. The input cellulose waste is gasified using steam in the absence of air and the primary gaseous products of carbon monoxide and hydrogen are subjected to heat, pressure, and catalysts to form methyl alcohol. Carbon monoxide is added to the methyl alcohol and further subjected to heat, pressure and catalysts to form acetic acid. The acetic acid is purified using a distillation tower, and removed for sale. Output production is increased by adding further carbon monoxide and hydrogen from burners used to heat the gasifiers. Further carbon monoxide and hydrogen are also produced by steam gasification of the carbon residue to promote a water/gas shift. These gases are fed into the gas stream produced by the gasification of cellulose, and provide more feedstock for the reactions. The three input gas streams arising from: 1) the steam gasification of cellulose; 2) the water/gas shift in the carbon reactor; and 3) the sub-stoichiometic oxygen burning of input burner gas to heat both retorts, maximize the output chemical production while reducing the consumption of energy needed for processing the cellulose and the carbon.

22 Claims, 10 Drawing Sheets

PROCESS FOR CONVERTING CELLULOSIC MATERIAL INTO LIQUIDS

CROSS REFERENCE TO RELATED PATENT APPLICATION

This patent application relates to U.S. Provisional Patent Application Serial No. 60/187,166 filed on Mar. 6, 2000 entitled Process for Producing Oxygenated $C_2$ Products from Biomass.

FIELD OF THE INVENTION

This invention relates to a process for converting biomass or cellulose material and in particular to converting-wood waste of various types into liquid hydrocarbons and in particularly acetic acid.

BACKGROUND OF THE INVENTION

Our civilization has been burdened with the products of modem living since the industrial revolution began. It has resulted in the defilement of the environment, and even natural product residues have contributed to the problems we now face.

For example, there has been over the years an accumulation of piles of wood waste from logging operations and the production of laminates, plywoods, furniture, dimensional lumber for buildings, and pallets. The pulp and paper industry can only utilize specific parts of a tree and therefore leaves considerable residue that to date has little use.

In addition to "clean" wood residues, there are many other types of wood residues which contain, or are coated with, paints, varnishes and chemicals: for example, demolished buildings or used and discarded wood from any source. These are more toxic to the environment because their on-board chemicals leach into the ground on which they sit.

The wood industry is very busy trying to find ways to utilize wood waste. A common alternate to landfill disposal is burning. Recently the industry has been focussing on using the heat from combusting wood waste to generate synthesis gas (syngas). Syngas is used to generate steam which is used to produce electrical power. But there is a disadvantage seldom emphasized, i.e. the large quantities of carbon dioxide produced and emitted into the atmosphere.

In addition, secondary industries have arisen to utilize wood waste, and these are the producers of particleboards, fiberboards, waferboards and extruded products. Other processes make animal bedding, animal litter, landscaping mulches, compost or ground covers. Some waste goes to erosion control.

Only a small percentage of wood waste is processed by the chemical industry. Some is used to produce methanol. Others utilize bacterial fermentation as a means of modifying wood residues into usable chemicals. These processes are relatively inefficient, with only the by-products of bacterial metabolism recovered. Enzymatic degradation of organic matter is a newer method to decompose the wood, but the economic viability of the process may be less than rewarding.

Accordingly, there exists a real need to utilize the cellulose waste to economically produce useful chemicals. Cellulose lends itself to reforming into the raw materials for plastics. Plastics are currently made using raw materials derived from petrochemical sources. In fact, we have relied heavily on the petrochemical industry to supply these raw materials. An efficient process to provide substantial volumes of these materials would have immediate positive impact on the world petrochemical industry. If indeed these materials could be produced at a lower cost, then not only would natural petroleum reserves be extended, but the economies of the plastic industry would shift in favour of the consumer.

A product with an extremely large world market such as acetic acid, would therefore be dramatically more lucrative than, for example, methanol since it is a raw material for the plastics industry. Additionally, chemical production with minimal greenhouse gas emissions would not only be economically more desirable, but environmentally more desirable. If wood waste is used to make raw materials for plastics, then the environment would be cleaned up and the world petroleum reserves would last longer.

SUMMARY OF THE INVENTION

A process for the production of acetic acid and other liquids from cellulose is disclosed. The cellulose is steam-gasified in the absence of air and the products consisting primarily of carbon monoxide and hydrogen are subjected to heat, pressure, and catalysts to form methyl alcohol. The methyl alcohol is mixed with carbon monoxide and subjected to heat, pressure and catalysts to form acetic acid and other liquids.

Additional carbon monoxide and hydrogen are generated from the burners using natural and unwanted process gas, under starved oxygen conditions, to provide heat for the gasifiers and additional feedstock for the conversion process. These gases are also added to the gases emerging from the gasification of the cellulose.

The carbon monoxide and hydrogen gases needed to make methyl alcohol and oxygenated $C_2$ products are, firstly separated in molecular sieves, secondly metered into the pressure vessels in the correct ratios to form the products. Small amounts of mixed hydrocarbon gases (CxHy) are also removed by the molecular sieves, and sent back to the burners to supplement the heating gas.

In a further enhancement of the process, carbon and fly ash particles are filtered from the gas stream after steam gasification of the cellulose, and heated with steam in the presence of a catalyst, to form carbon monoxide and hydrogen. These gases are sent to the molecular sieves to be separated, and used subsequently in the pressure vessels to add to the products formed.

The final product liquid is run through an oil/water separator to remove water, then sent to a distillation tower where it is purified and removed from the system for sale. Any extraneous hydrocarbons which emerge from the distillation process, most of which is formed in the first pressure vessel, are sent back to the initial reactor to be re-processed with new cellulose input.

The three input gas streams arising from: 1) the steam gasification of cellulose; 2) the water/gas shift in the carbon reactor; and 3) the sub-stoichiometric oxygen burning of input burner gas to heat both retorts, maximize the output chemical production while reducing the consumption of energy needed for processing the cellulose and the carbon.

Further features of the invention will be described or will become apparent in the course of the following detailed description.

BRIEF DESCRIPTION OF THE DRAWINGS

The invention will now be described by way of example only, with reference to the accompanying drawings, in which.

DETAILED DESCRIPTION OF THE INVENTION

Figure 1:
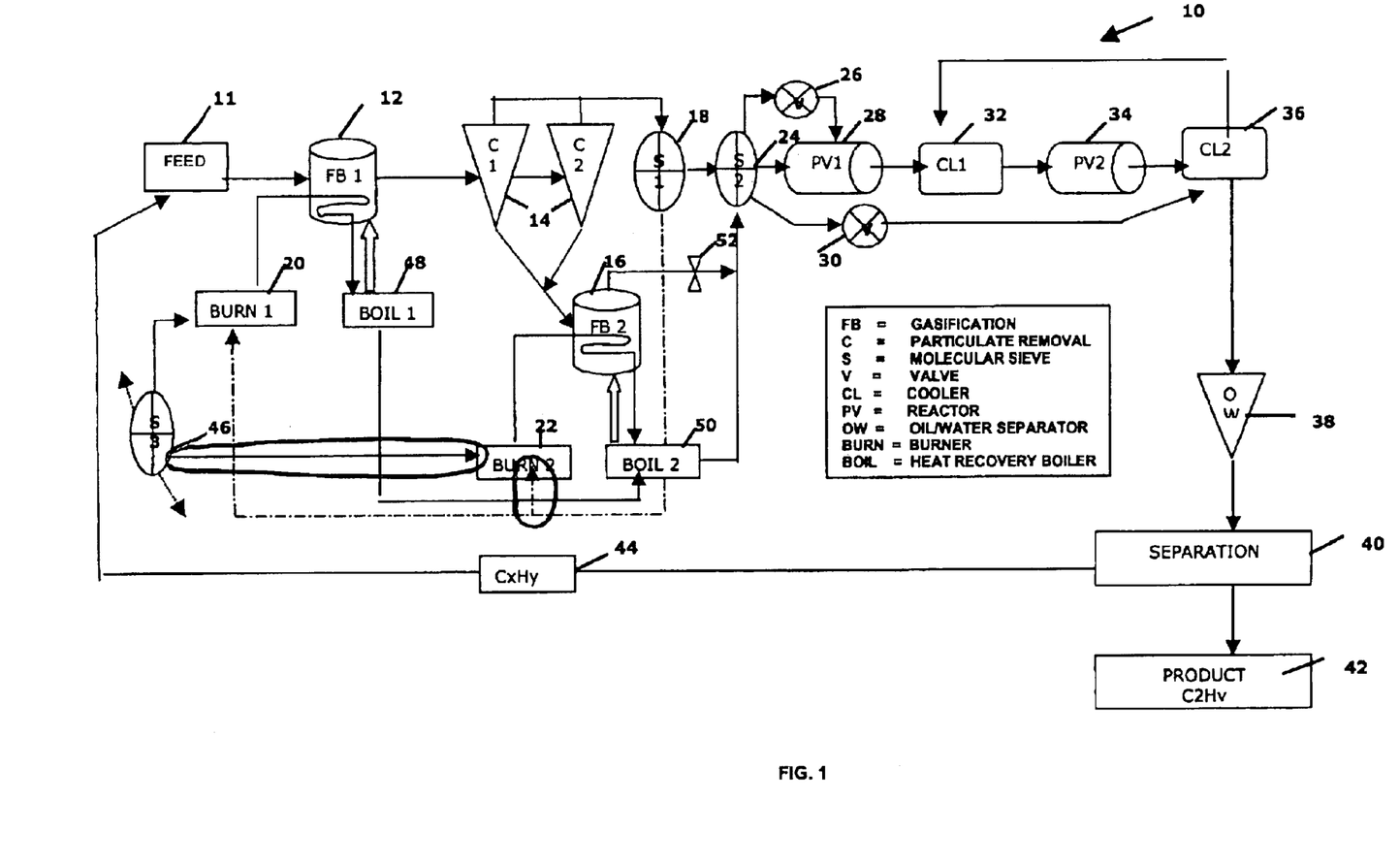
FIG. 1 is a schematic diagram of the equipment and process flow of the process for producing acetic acid of the present invention.

Referring to FIG. 1, the process for producing acetic acid from celluose waste is shown generally at 10. It will be appreciated by those skilled in the art that the process disclosed herein is disclosed in terms of ideal conditions as the conditions in the system fluctuate the gases and liquids that are produced will vary.

Cellulose material or wood waste 11 is fed into a first retort 12 and heat is applied to gasify the molecules. Typically the temperature of the material is raised to between 650 and 900° C. and preferably it is raised to 675° C. First retort 12 is a closed vessel whereby air is excluded and the pressure is kept at sufficient slight sub-atmospheric pressure to maximize the gasification. One alternative is that the first retort 12 is a heated fluid bed type system. Preferably the pressure is maintained between 14.5 and 12 psi. Steam is infused into first retort 12 in the amount required to optimize the formation of $H_2O$, CO and $H_2$ to minimize the formation of $CH_4$ and $CO_2$. The gas stream thus generated is largely carbon monoxide (CO) and hydrogen ($H_2$) with very small amounts of other hydrocarbons (CxHy) and some carbon dioxide ($CO_2$). The gas stream carries with it particulate including fly ash and carbon. The gas stream is cleaned to remove the particulate. One option shown herein is to send the gas through a series of two cyclones 14, in which the particulate is removed and sent to a second retort 16, described in more detail below. Alternatively the gas could be cleaned with electrostatic precipitators or bag houses.

The cleaned gas stream enters a molecular sieve 18 to remove the larger hydrocarbons (CxHy) (19) from the CO and $H_2$. These CxHy are directed into first burner 20 or second burner 22 to supplement the heating gases therein. The other gases emerging from molecular sieve 18 enter a second sieve 24, which separates the carbon monoxide (CO) from the hydrogen ($H_2$). The $H_2$ is sent through a hydrogen metering valve 26 and enters a first pressure vessel 28. The CO is sent through a carbon monoxide metering valve 30. The gases are metered such that the quantity of gases are generally in a ratio 2:1 of $H_2$ to CO.

In first pressure vessel 28 the gases are heated to temperatures typically between 200–300° C. at pressures between 50–150 atmospheres in the presence of catalysts to achieve maximum conversion of the carbon monoxide and hydrogen mixture into methanol. To date, the most efficient catalysts have been shown to be $Cu$—$ZnO$—$Al_2O_3$, a copper zinc oxide on an aluminium base. In the first pressure vessel 28 methanol is formed, plus minor amounts of hydrocarbons, higher alcohols, ethers, ketones and esters. These liquids are in gaseous form and are sent to a first cooler 32 where they are condensed and are then sent to a second pressure vessel 34.

In second pressure vessel 34 the condensates are blended with CO from molecular second sieve 24. Preferably methanol and CO are combined in a ratio of 1:1. The material in second pressure vessel 34 are typically heated to 150–200° C. at pressures of between 3365 atmospheres in the presence of a catalyst. Catalyst such as a combination of rhodium, phosphine and iodine (in the form of HI, MeI or $I_2$) are used to produce acetic acid. These conditions are selected to maximize the reaction of the methyl alcohol to form acetic acid. The resulting products are in gaseous form, and include the acetic acid plus the other products previously referred to that were formed in first pressure vessel 28. The gas stream is sent to second cooler 36 where the liquid products condense specifically acetic acid. It will be appreciated by those skilled in the art that the predominant liquid will be acetic acid but other liquid products may also be present.

The liquids are sent to an oil/water separator 38 where the hydrocarbons are separated from any water. The water is recycled back into the system. The remaining liquids are sent to a distillation tower 40, and acetic acid 42 is removed. The other liquid products 44 are not separated from each other, but are sent to the feed 11 and are fed into first retort 12 to be reprocessed.

First retort 12 is a fluid bed system that is indirectly heated using hot gases from first burner 20. Typically the material is heated to between 650° C. and 900° C. and preferably 675° C. The burner is supplied with oxygen which is derived from a third molecular sieve 46 and utilizes methane (or natural gas). The burner is operated with volumes of oxygen to provide starved oxygen (sub-stoichiometric) conditions to produce as much carbon monoxide (CO) and hydrogen ($H_2$) and as little carbon dioxide ($CO_2$) and hydrocarbons such as methane ($CH_4$) as possible. The hot gases are used to heat the retort, then are sent to a first heat recovery boiler 48 which heats water to make steam to feed into first retort 12. As discussed earlier, this minimizes the production of $CO_2$ and small hydrocarbons. The gases that emerge from the first heat recovery boiler 48 are sent to second heat recovery boiler 50.

The carbon and fly ash removed by the cyclones 14 are fed into second retort 16. Steam is supplied to the retort 16 by second heat recovery boiler 50 and the contents therein are heated to temperatures sufficient, typically between 400–500° C. at typically 3–15 atmospheres, to cause a water/gas shift to occur and form a maximum amount of carbon monoxide (CO) and hydrogen ($H_2$). This gas is commonly referred to as Synthesis gas. The gases are then fed into a pressure equalizer 52 prior to entering second molecular sieve 24. The gas streams emerging from molecular sieve 24 are joined by gases from molecular sieve 18 and first and second heat recovery boilers 48 and 50.

Second retort 16 is indirectly heated using hot gases from second burner 22. The second burner 22 utilizes methane (or natural gas) plus CxHy from first molecular sieve 18 and is supplied with sufficient oxygen from second molecular sieve 24 to produce sub-stoichiometric (starved) oxygen conditions to produce carbon monoxide (CO) and hydrogen ($H_2$). These hot gases are used to indirectly heat the retort then are sent to the second heat recovery boiler 50 which heats water to make steam. The spent gases from this loop are then sent to second molecular sieve 24 where they are separated.

Figure 2:
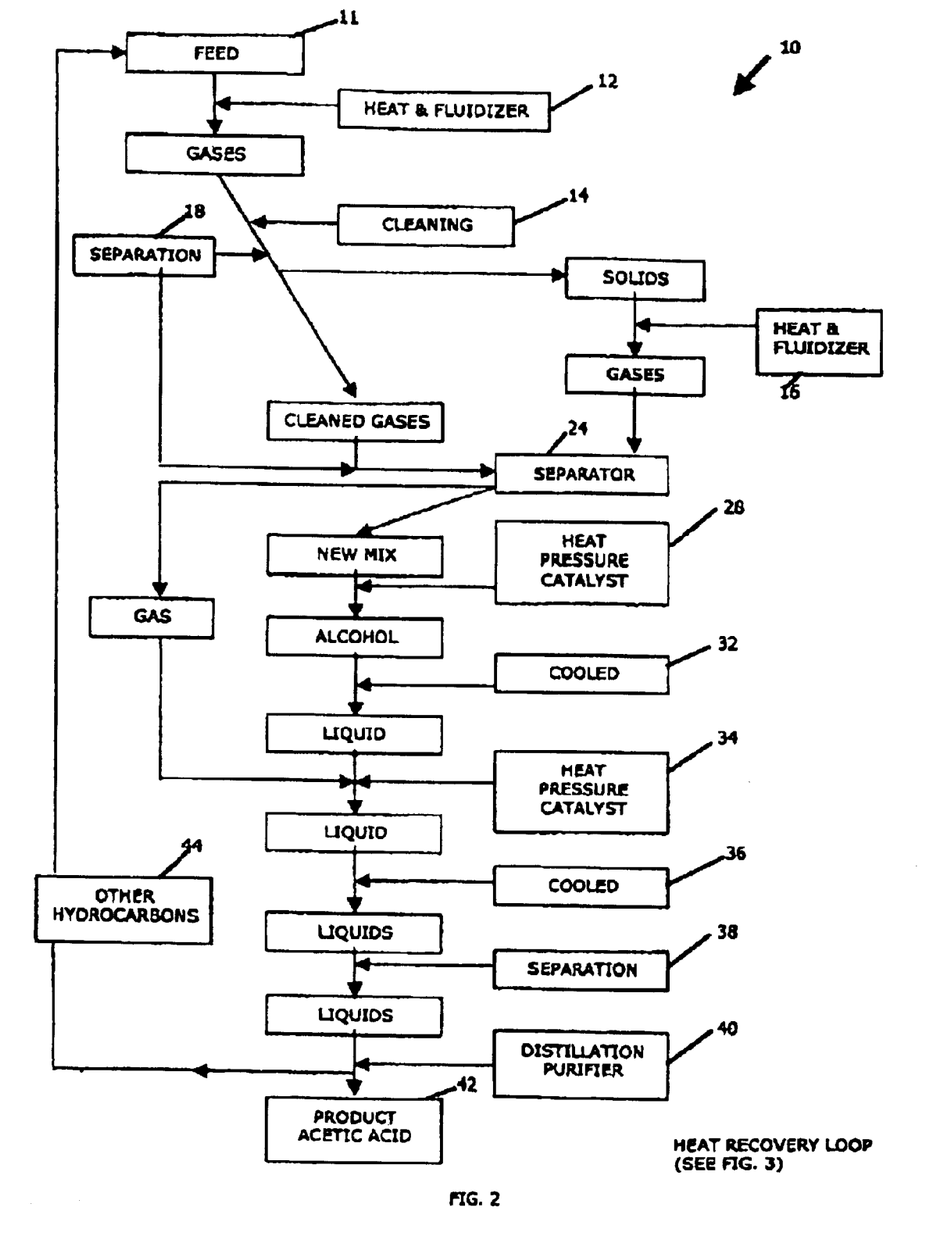
FIG. 2 is a flow diagram of materials and their progression through the process for producing acetic acid of the present invention.
Figure 3:
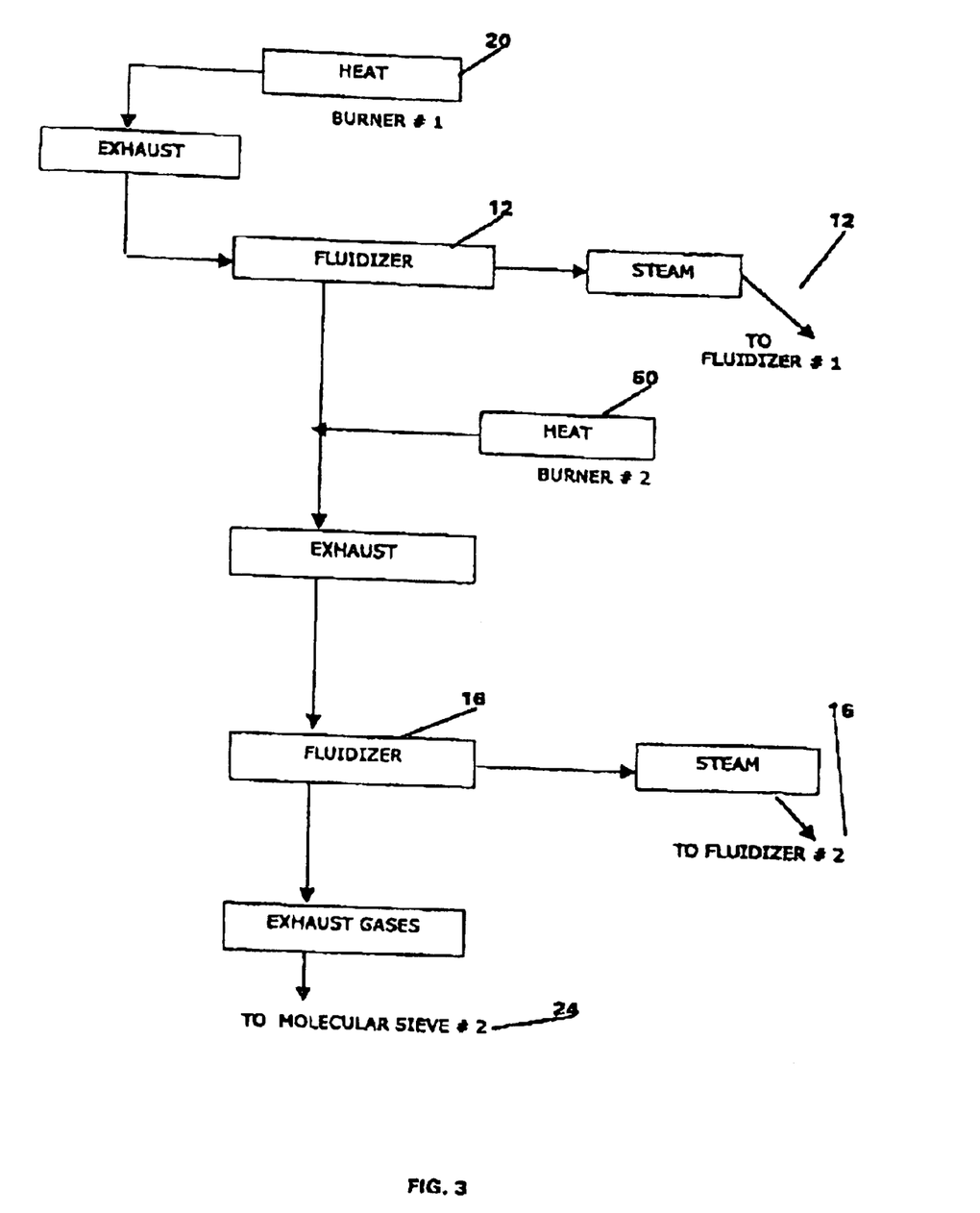
FIG. 3 is a flow diagram of the heat recovery loop portion of the process of the present invention.

Referring to FIGS. 2 and 3, the above process is shown in a flow diagram form.

Figure 4:
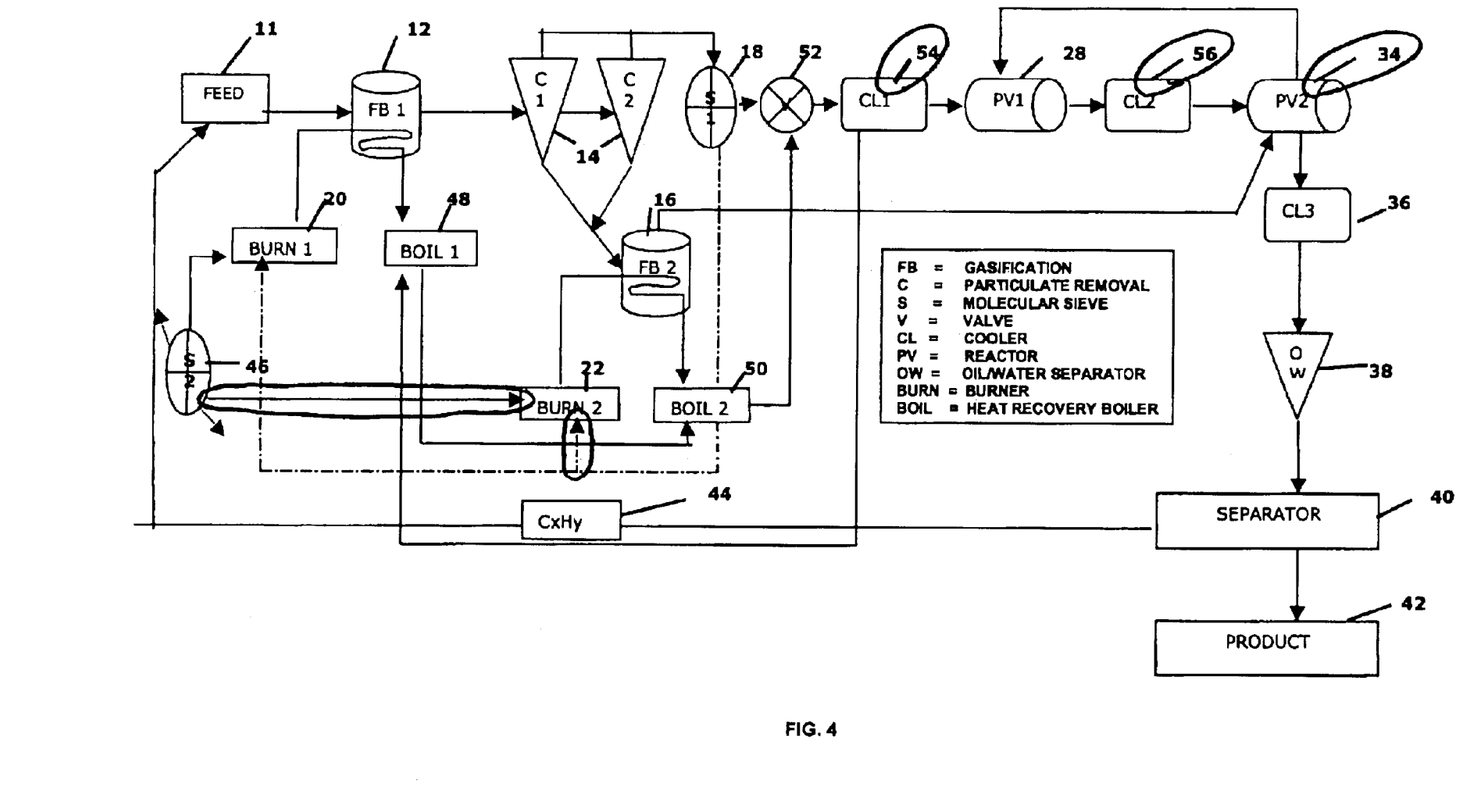
FIG. 4 is a schematic diagram of an alternate embodiment of the equipment and process flow of the process for producing acetic acid of the present invention.

An alternate process is shown in FIG. 4 wherein only those portions that are different will be provide with different reference numbers and described herein. In this embodiment the second molecular sieve is not used, allowing CO and $H_2$ into the first pressure vessel 28 without being metered. The gases, mostly CO and $H_2$, from the water/gas shift in second retort 16 are fed directly into the second pressure vessel 34. Extraneous $H_2$ not consumed in the reaction to form acetic acid in second pressure vessel 34 is send back to first pressure vessel 28 to be used in the formation of methanol. A chiller 54 cools the gases emerging from the first molecular sieve 18 and water is condensed out and is sent back to first heat recovery boiler 48. Exhaust gases from the partial combustion of heating gases from second heat recovery boiler 50 are sent to join the gas stream emerging from the first molecular sieve 18.

It will be appreciated that the above description related to embodiments by way of example only. Many variations on the invention will be obvious to those skilled in the art and such obvious variations are within the scope of the invention as described herein whether or not expressly described.

CHEMISTRY

In theory, cellulose breaks down under steam gasification to yield carbon monoxide and hydrogen gases.
The balanced equation for the reaction is:

(cellulose) (carbon monoxide+hydrogen+carbon)

Under ideal conditions, this breakdown is complete, and no other products are formed. However, if the input contains other organic or inorganic molecules, the breakdown will result in other compounds. Wood, by it's nature, does contain other molecules.
The "real world" equation, therefore is:

$C_6H_{10}O_5 + CxHy \rightarrow 5CO + 5H_2 + CxHy + C$

Other reactions in the process are:

The above description relates to one possible use of the process. However, the general principles shown herein could be used to produce other liquids. For example the catalysts could be changed and some further gases introduced to produce liquids such as formaldehyde or urea-formaldehyde. Alternatively the process could be optimized to produce methanol. It will be appreciated that minor variations could be used to produce a wide variety of liquid products and all such variations are considered within the scope of this invention. Hereafter a general process will be discussed with some specific alternatives.

Figure 5:
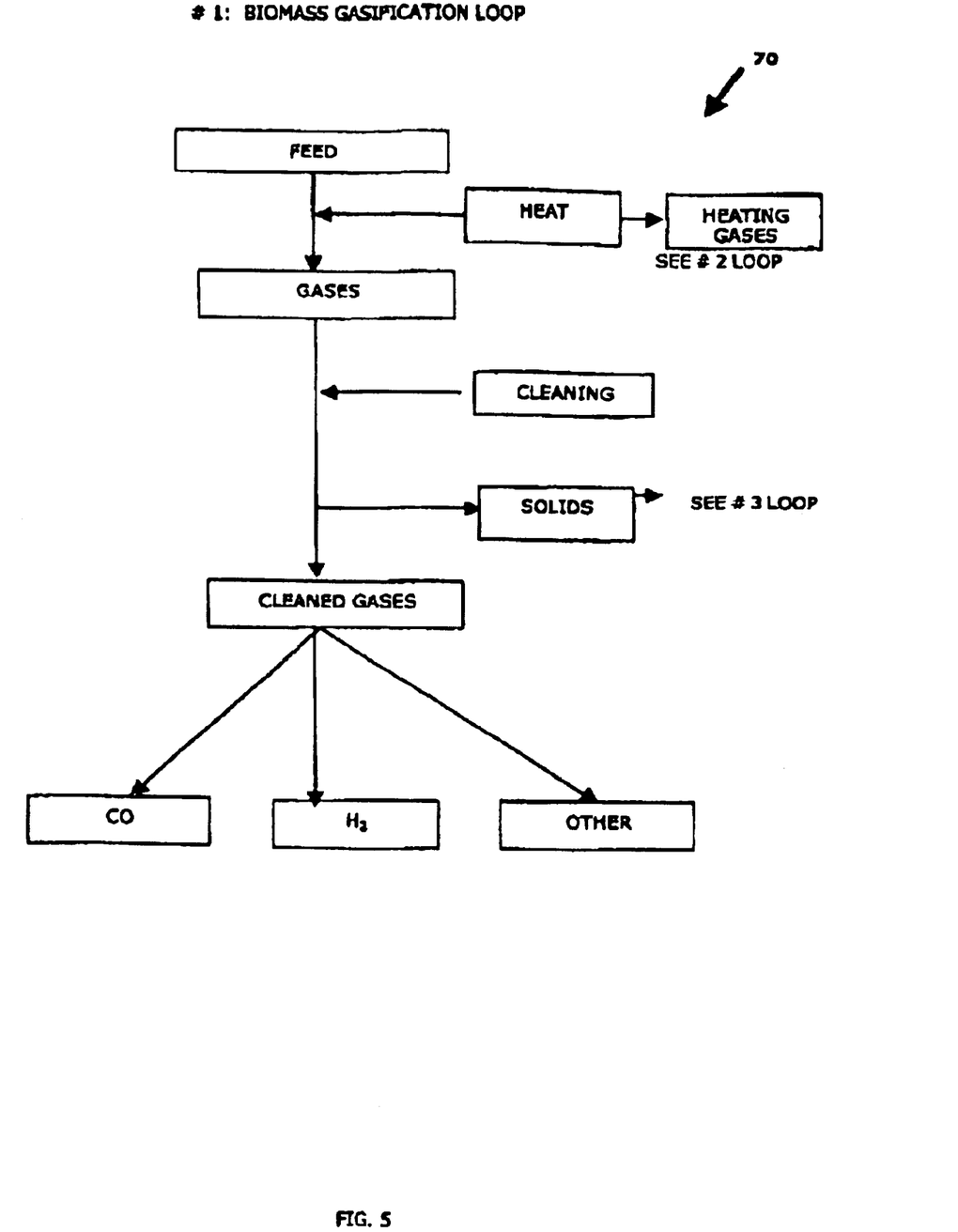
FIG. 5 is a flow diagram of the biomass volatization loop portion of the process of the present invention.
Figure 6:
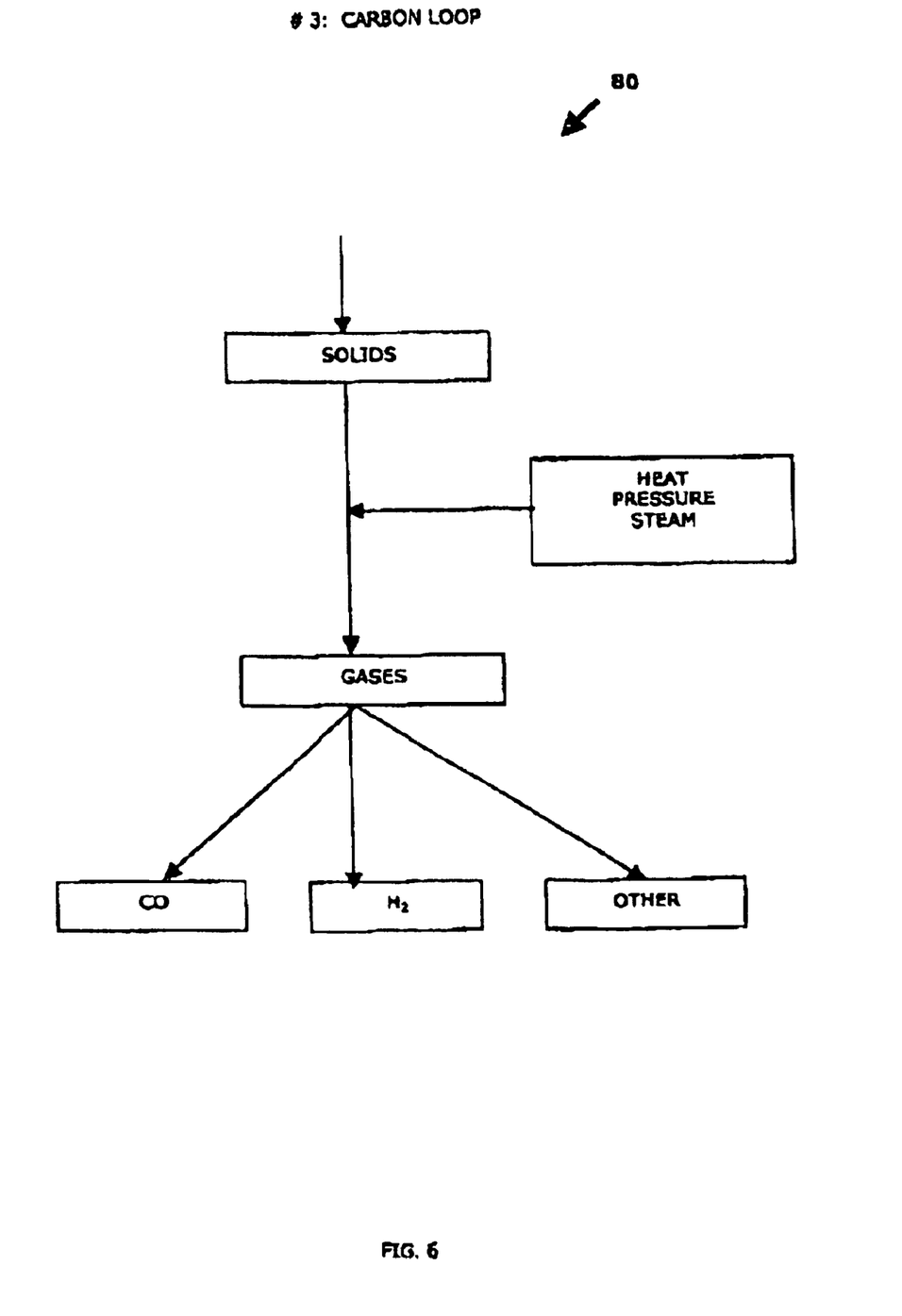
FIG. 6 is a flow diagram of carbon volatization loop portion of the process of the present invention.
Figure 7:
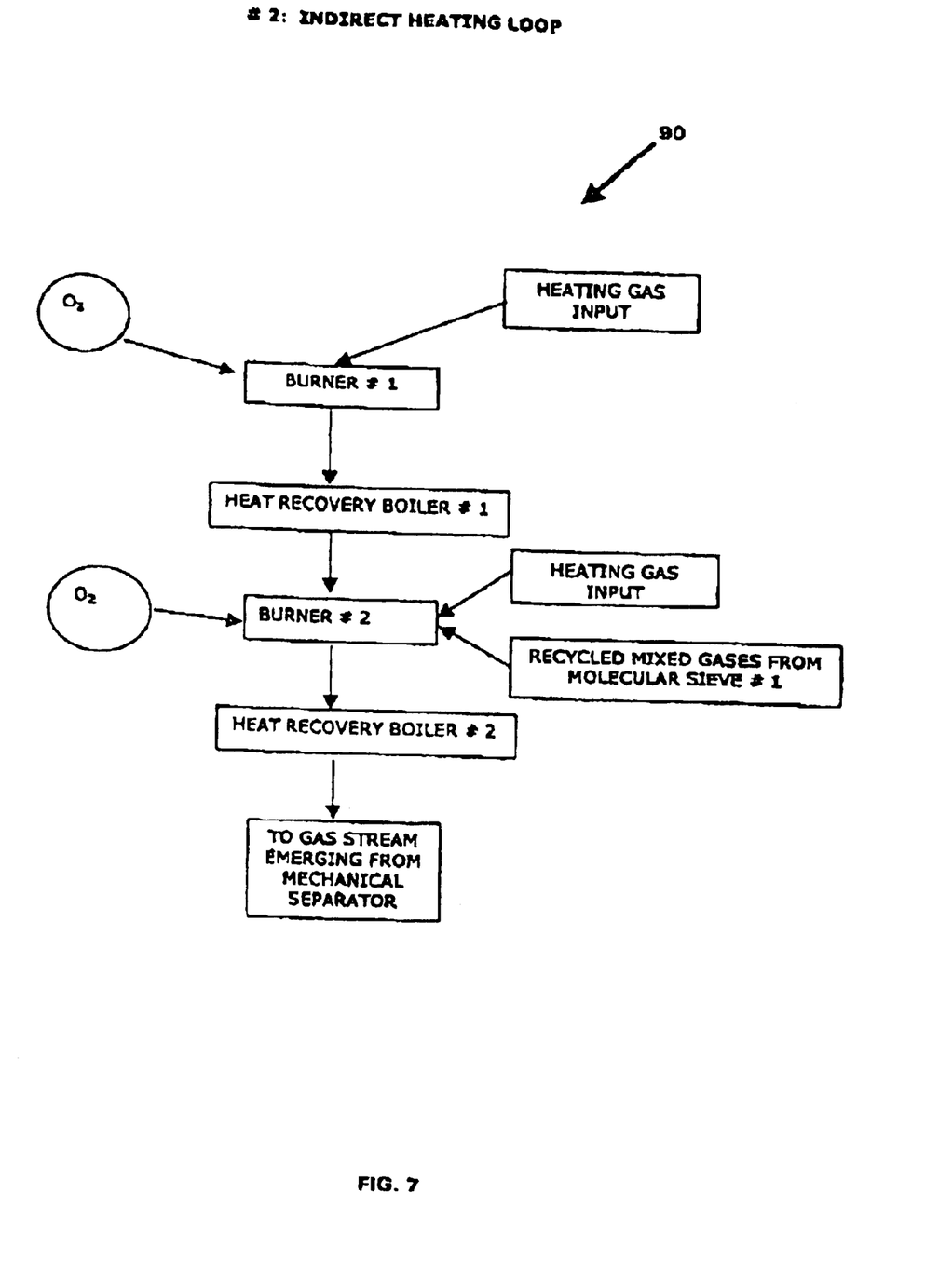
FIG. 7 is a flow diagram of the indirect heating loop portion of the process of the present invention.

Referring to FIGS. 5, 6 and 7 there are a number of methods to provide the required gases. All of the systems are designed to turn cellulosic material into salable liquids. Accordingly the main source of gaseous inputs is shown in FIG. 5 wherein the biomass waste is volatized. In addition carbon waste which is a bi-product of the biomass process can be used to create needed input gases and that process is shown in FIG. 6. In addition gases from the indirect heating loop can also be used as input gases and that process is shown in FIG. 7.

Referring to FIG. 5 a flow diagram showing the volatization of the biomass is shown generally at 70. The Cellulosic materials are pretreated by chipping to a size which is maximum two inches in diameter, then dried to extract moisture until the material contains less than 10% moisture content. The material is fed by a continuous feed mechanism into the heating vessel (retort) and heat is applied to raise the temperature of the material to between 650 and 900° C., preferably to 675° C. The feed injection is done in a manner which excludes air from ingressing. Steam is infused continuously into the retort in a quantity calculated to optimize the cracking of the material into the fragments of CO and $H_2$ and minimize the formation of $CO_2$ and larger hydrocarbon molecules.

The gas stream thus formed by the cracking of the cellulosic materials are drawn out of the retort, which is kept at slightly less then atmospheric pressure. The hot gas stream is passed through mechanical separators such as cyclones, electrostatic precipitators or a bag house to remove carbon and any other particulate matter which has been formed in the cracking process. The cleaned gases are then processed further, as described.

Referring to FIG. 6 the carbon volatization loop is shown generally at 80. Carbon particulate material which is removed from the mechanical precipitators in the cellulosic cracking process described collected and sent to a second indirectly heated retort. Steam is supplied to the retort by a second heat recovery boiler and the gases therein are heated to temperatures sufficient, typically between 400–500° C. at typically 3–15 atmospheres, to cause a water/gas shift to occur and form a maximum amount of carbon monoxide (CO) and hydrogen ($H_2$). This gas is commonly referred to as Synthesis gas (syngas). The gases are then fed into a pressure equalizer prior to entering second molecular sieve.

Referring to FIG. 7, the indirect heating loop is shown generally at 90. The burner for the first heated retort, used to crack the cellulosic materials, is supplied with oxygen which is derived from a molecular sieve and utilizes methane (or natural gas). The burner is operated with volumes of oxygen to provide starved (sub-stoichiometric) conditions to produce as much carbon monoxide (CO) and hydrogen ($H_2$) and as little carbon dioxide ($CO_2$) as possible. The hot gases are used to indirectly heat the retort then are sent to a first heat recovery boiler which heats water to make steam to be fed into first retort to supply limited oxygen to the cellulose material. As discussed earlier, this minimizes the production of $CO_2$. The gases that emerge from the first heat recovery boiler are sent to second heat recovery boiler.

The second retort used to process the carbon particulates removed from the mechanical separators is indirectly heated using hot gases from a second burner. The second burner utilizes methane (or natural gas) plus CxHy from first molecular sieve and is supplied with sufficient oxygen from second molecular sieve to produce sub-stoichiometric (starved) oxygen conditions to produce carbon monoxide (CO) and hydrogen ($H_2$). These hot gases are used to indirectly heat the retort then are sent to the second heat recovery boiler which heats water to make steam. The spent gases from this loop are then sent to join the gases emerging from the mechanical separator Referring to FIG. 8 a first variation of the process is shown generally at 100 wherein the gas produced is methanol. A representative aliquot of the cleaned gas stream 102 is measured on its way to the pressure vessel. A calculated volume of the gas stream is diverted into a molecular sieve to separate 104 the CO 106 from the $H_2$ 108 according to the amount of $H_2$ needed in the correct ratio to CO in the pressure vessel to form methanol 110. The $H_2$ is sent to the pressure vessel, and the CO 106 is reacted with water 112 to form $CO_2$ 114 and $H_2$ 116. The $H_2$ is sent to the pressure vessel to complete the requirement for methanol 110 formation. The $CO_2$ is vented to the atmosphere, or collected for resale.

Figure 8:
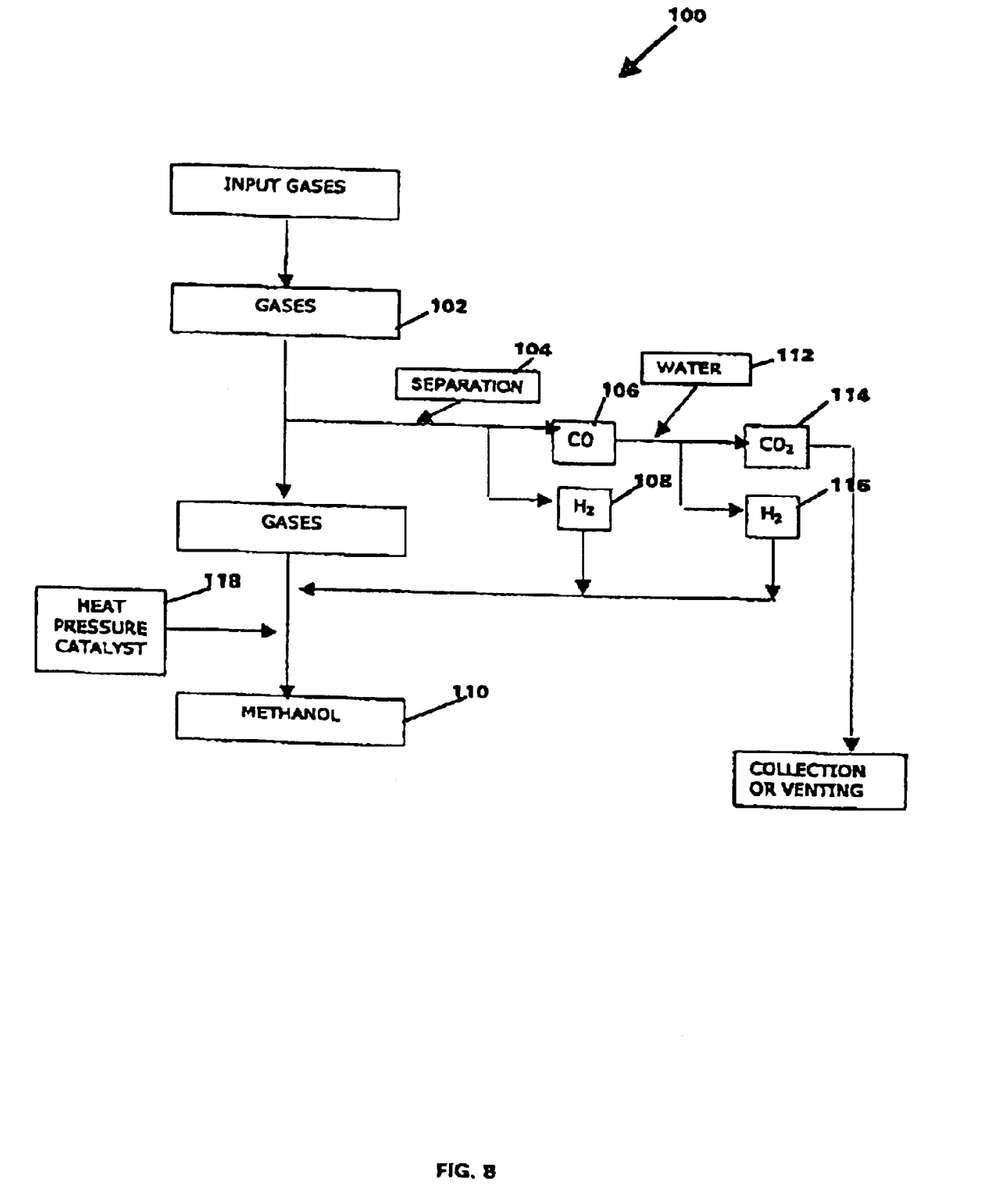
FIG. 8 is a flow diagram of the process of the present invention wherein methanol is produced.

The gas mix in the vessel are subjected to pressure of 50–100 atmospheres at 220–250° C. The catalyst 118 is selected from copper based, zinc oxide with another oxide such as alumina or chromia, or others shown to be more effective.

Figure 9:
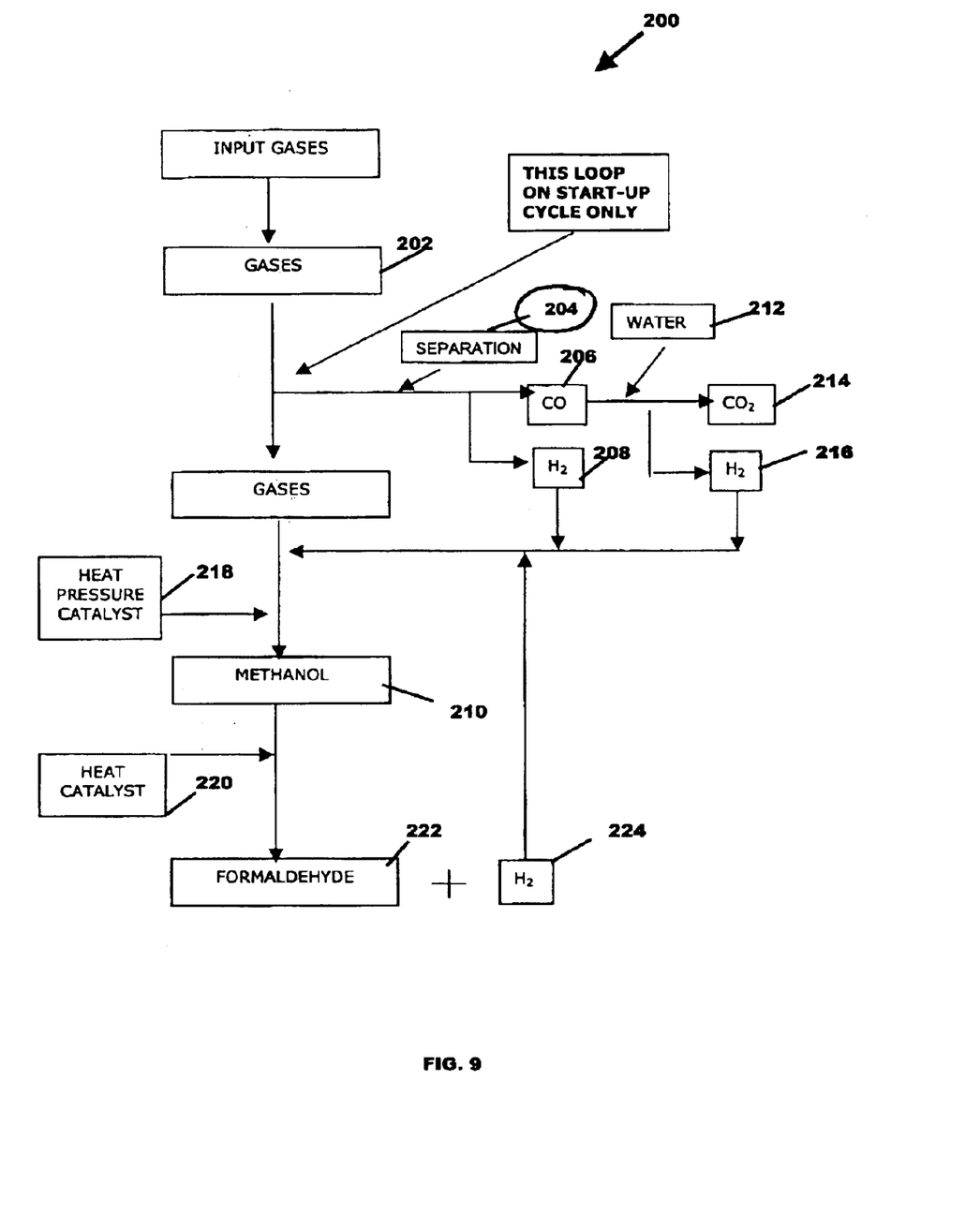
FIG. 9 is a flow diagram of the process of the present invention wherein formaldehyde is produced.

Referring to FIG. 9 a second variation of the process is shown generally at 200 wherein the gas produced is formaldehyde. A representative aliquot of the cleaned gas stream is measured on its way to the pressure vessel. A calculated volume of the gas stream 202 is diverted into a molecular sieve to separate 204 the CO 206 from the $H_2$ 208, according to the amount of $H_2$ needed in the correct ratio to CO in the pressure vessel to form methanol 210. The $H_2$ is sent to the pressure vessel, and the CO is reacted with water 212 to form $CO_2$ 214 and $H_2$ 216. The $H_2$ is sent to the pressure vessel in the presence of a catalyst 218 to complete the requirement for methanol formation. The $CO_2$ is vented to the atmosphere, or collected for resale.

The methanol formed is sent to a second reactor in vapor form, in which a stationary bed silver catalyst 220 is used, and heat of 700° C. is applied. A small amount of air is allowed into the vessel to promote the reaction, and formaldehyde 222 is formed. A small amount of $H_2$ 224 gas remains which is sent back and utilized in the methanol reaction vessel. It should be noted that the a volume of the gas stream 202 only needs to be diverted in the start up phase because thereafter $H_2$ 224 can be used.

Figure 10:
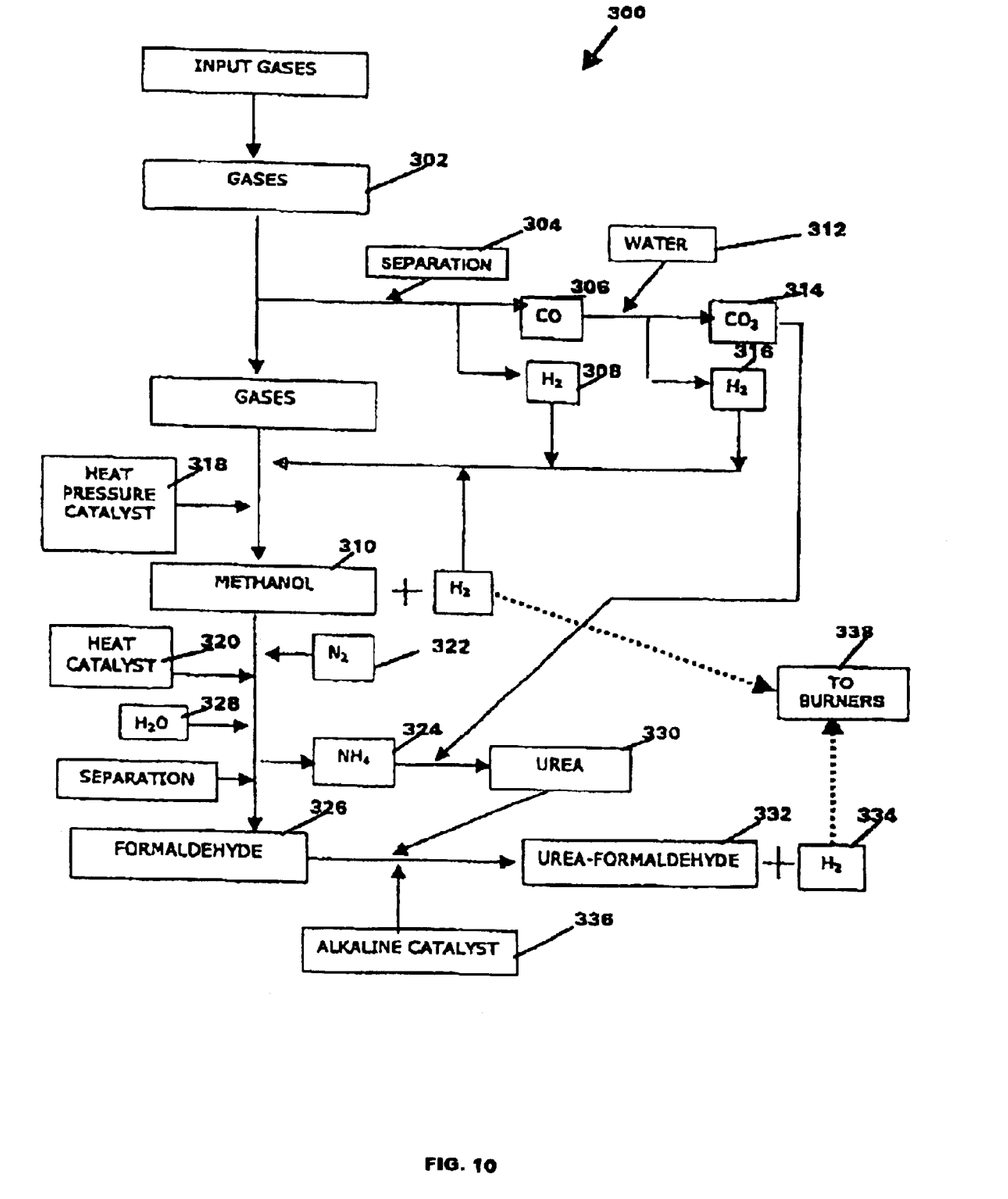
FIG. 10 is a flow diagram of the process of the present invention wherein urea-formaldehyde is produced.

Referring to FIG. 10 a third variation of the process is shown generally at 300 wherein the gas produced is urea-formaldehyde. A representative aliquot of the cleaned gas stream 302 is measured on its way to the pressure vessel. A calculated volume of the gas stream is diverted into a molecular sieve to separate 304 the CO 306 from the $H_2$ 308, according to the amount of $H_2$ needed in the correct ratio to CO in the pressure vessel to form methanol 310. The $H_2$ is sent to the pressure vessel, and the CO is reacted with water 312 to form $CO_2$ 314 and $H_2$ 316. The $H_2$ is sent to the pressure vessel to complete, in the presence of a catalyst 318, the requirement for methanol 310 formation. The $CO_2$ is sent to the third reaction vessel to be used in the urea-formaldehyde formation.

The methanol 310 formed is sent to a second reactor in vapor form, in which a silver catalyst 320 is used and heat of 700° C. is applied, Atmospheric nitrogen 322 is fed into the vessel, and ammonia ($NH_4$) 324 and formaldehyde 326 are formed. Water 328 is added to dissolve the formaldehyde 326, leaving the ammonia 324 in vapor form. The $NH_4$ 324 is sent to a third reactor to which the $CO_2$ 314 from the steps above is added. Urea 330 then forms, which is sent to a fourth reactor together with the formaldehyde 326 and water 328. The mixture of formaldehyde 326 and urea 330 react to form urea-formaldehyde 332 and $H_2$ 334. The reaction is catalysed 336 by a slightly alkaline reactant which is selected on the basis of selectivity. The $H_2$ 334 is sent back to the methanol vessel if needed for more methanol formation, or if there is excess, fed into the primary burner 338 to supply heat to the initial cellulosic materials gasification step.

It will be appreciated that the above description related to the invention by way of example only. Many variations on the invention will be obvious to those skilled in the art and such obvious variations are within the scope of the invention as described herein whether or not expressly described.

What is claimed is:

1. A process for producing acetic acid from cellulosic material comprising the steps of:
   heating the cellulosic material to a temperature between 650 and 900° C. at a pressure between 12 and 14.5 psi, generally in the absence of oxygen to crack the material and introducing steam thereby producing a gas stream, the gas stream including fly ash, carbon, carbon monoxide and hydrogen, wherein at least a majority of the heating is indirect heating;
   cleaning the gas stream to remove fly ash and carbon thereby producing a cleaned gas stream;
   separating the gases in the cleaned gas stream to remove the carbon monoxide and hydrogen gases therefrom;
   metering each of the hydrogen and the carbon monoxide in a predetermined ratio into a first heated pressure vessel with a catalyst to form methanol;
   condensing the methanol to produce a condensate and passing the condensate into a second heated pressure vessel with a catalyst and carbon monoxide to form acetic acid; and
   condensing the acetic acid and other material present and removing the acetic acid from water and other products therein thereby purifying the acetic acid.

2. A process for producing acetic acid from cellulosic material as claimed in claim 1 wherein the predetermined ratio of hydrogen to carbon monoxide is 2:1.

3. A process for producing acetic acid from cellulosic material as claimed in claim 2 wherein the heating temperature is 675° C.

4. A process for producing acetic acid from cellulosic material as claimed in claim 2 further including the steps of:
   heating the carbon and fly ash removed from the gas stream in the presence of steam thereby producing gases from carbon gasification;
   equalizing the pressure of the gases emerging from the carbon gasification using a pressure equalizer thereby producing equalized gases;
   directing the equalized gases to a molecular sieve and separating carbon monoxide and hydrogen therefrom and directing each to the metering step.

5. A process for producing acetic acid from cellulosic material as claimed in claim 4 wherein indirect heat is provided during the step of heating the carbon and fly ash by at least one burner under starved oxygen conditions.

6. A process for producing acetic acid from cellulosic material as claimed in claim 5 wherein carbon monoxide and hydrogen are produced in each burner and further including the steps of cooling the carbon monoxide and hydrogen from the burners and adding each to the metering step.

7. A process for producing acetic acid from cellulosic material as claimed in claim 1 wherein fluid bed retorts are used in the heating step.

8. A process for producing acetic acid from cellulosic material as claimed in claim 1 wherein the step of separating the gases in the cleaned gas stream is by way of a molecular sieve.

9. A process for producing a liquid from cellulosic material comprising the steps of:
heating the cellulosic material to a temperature between 650 and 900° C. at a pressure between 12 and 14.5 psi, generally in the absence of oxygen to crack the material and introducing steam thereby producing a gas stream, the gas stream including fly ash, carbon, carbon monoxide and hydrogen, where in at least a majority of the heating is indirect heating;
cleaning the gas stream to remove fly ash and carbon thereby producing a cleaned gas stream;
separating the gases in the cleaned gas stream to remove the carbon monoxide and hydrogen gases therefrom;
metering each of the hydrogen and the carbon monoxide in a predetermined ratio into a heated pressure vessel with a catalyst to form a liquid product.

10. A process for producing a liquid from cellulosic material as claimed in claim 9 wherein the liquid product is methanol and the catalyst is copper zinc oxide on aluminium base.

11. A process for producing a liquid from cellulosic material as claimed in claim 10 further including the steps of introducing a second catalyst to the methanol to produce a second liquid product.

12. A process for producing a liquid from cellulosic material as claimed in claim 11 wherein the second liquid product is formaldehyde and the second catalyst is silver.

13. A process for producing a liquid from cellulosic material as claimed in claim 12 further including the steps of the introducing nitrogen, ammonia, water to the formaldehyde to produce urea-formaldehyde.

14. A process for producing a liquid from cellulosic material as claimed in claim 11 wherein the second liquid product is acetic acid and the second catalyst is chosen from the group consisting of a combination of rhodium, phosphine and iodine.

15. A process for producing acetic acid from cellulosic material as claimed in claim 1 wherein the heating step takes place generally at atmospheric pressure.

16. A process for producing acetic acid from cellulosic material as claimed in claim 9 wherein the heating step takes place generally at atmospheric pressure.

17. A process for producing acetic acid from cellulosic material comprising the steps of:
indirectly heating the cellulosic material to a temperature between 650 and 900° C. at a pressure between 12 and 14.5 psi, generally in the absence of oxygen to crack the material and introducing steam thereby producing a gas stream, the gas stream including fly ash, carbon, carbon monoxide and hydrogen;
cleaning the gas stream to remove fly ash and carbon thereby producing a cleaned gas stream;
separating the gases in the cleaned gas stream to remove the carbon monoxide and hydrogen gases therefrom;
metering each of the hydrogen and the carbon monoxide in a predetermined ratio into a first heated pressure vessel with a catalyst to form methanol;
heating the carbon and fly ash removed from the gas stream in the presence of steam thereby producing gases from carbon gasification;
equalizing the pressure of the gases emerging from the carbon gasification using a pressure equalizer thereby producing equalized gases;
directing the equalized gases to a molecular sieve and separating carbon monoxide and hydrogen therefrom and directing each to the metering step;
condensing the methanol to produce a condensate and passing the condensate into a second heated pressure vessel with a catalyst and carbon monoxide to form acetic acid; and
condensing the acetic acid and other material present and removing the acetic acid from water and other products therein thereby purifying the acetic acid.

18. A process for producing acetic acid from cellulosic material as claimed in claim 17 wherein indirect heat is provided during the step of heating the carbon and fly ash by at least one burner under starved oxygen conditions.

19. A process for producing acetic acid from cellulosic material as claimed in claim 18 wherein carbon monoxide and hydrogen are produced in each burner and further including the stops of cooling the carbon monoxide and hydrogen from the burners and adding each to the metering step.

20. A process for producing acetic acid from cellulosic material comprising the steps of:
indirectly heating the cellulosic material to a temperature between 650 and 900° C. at a pressure between 12 and 14.5 psi, generally in the absence of oxygen to crack the material and introducing steam thereby producing a gas stream, the gas stream including fly ash, carbon, carbon monoxide and hydrogen, wherein fluid bed retorts are used in the heating step;
cleaning the gas stream to remove fly ash and carbon thereby producing a cleaned gas stream;
separating the gases in the cleaned gas stream to remove the carbon monoxide and hydrogen gases therefrom;
metering each of the hydrogen and the carbon monoxide in a predetermined ratio into a first heated pressure vessel with a catalyst to form methanol;
condensing the methanol to produce a condensate and passing the condensate into a second heated pressure vessel with a catalyst and carbon monoxide to form acetic aid; and
condensing the acetic acid and other material present and removing the acetic acid from water and other products therein thereby purifying the acetic acid.

21. A process for producing acetic acid from cellulosic material comprising the steps of:
indirectly heating the cellulosic material to a temperature between 850 and 900° C. at a pressure between 12 and 14.5 psi, generally in the absence of oxygen to crack the material and introducing steam thereby producing a gas stream, the gas stream including fly ash, carbon, carbon monoxide and hydrogen;
cleaning the gas stream to remove fly ash and carbon thereby producing a cleaned gas stream;
separating the gases in the cleaned gas stream to remove the carbon monoxide and hydrogen gases therefrom;
metering each of the hydrogen and the carbon monoxide in a predetermined ratio into a first heated pressure vessel with a catalyst to form methanol;
condensing the methanol to produce a condensate and passing the condensate into a second heated pressure vessel with a catalyst and carbon monoxide to form acetic acid; and
condensing the acetic acid and other material present and removing the acetic acid from water and other products therein thereby purifying the acetic add, wherein the step of separating the gases in the cleaned gas stream is by way of a molecular sieve.

22. A process for producing liquid products from cellulosic material comprising the steps of:

indirectly heating the cellulosic material to a temperature between 650 and 900° C. at a pressure between 12 and 14.5 psi, generally in the absence of oxygen to crack the material and introducing steam thereby producing a gas stream, the gas stream including fly ash, carbon, carbon monoxide and hydrogen;

cleaning the gas stream to remove fly ash and carbon thereby producing a cleaned gas stream;

separating the gases in the cleaned gas stream to remove the carbon monoxide and hydrogen gases therefrom;

metering each of the hydrogen and the carbon monoxide in a predetermined ratio into a heated pressure vessel with copper zinc oxide on aluminium base to form methanol, introducing silver to the methanol to produce formaldehyde, and introducing nitrogen, ammonia water to the formaldehyde to produce urea-formaldehyde.

* * * * *